United States Patent [19]

Warriner

[11] Plant 3,995

[45] Dec. 21, 1976

[54] ROSE PLANT

[75] Inventor: William A. Warriner, Tustin, Calif.

[73] Assignee: Jackson & Perkins Company, Medford, Oreg.

[21] Appl. No.: 622,845

[22] Filed: Oct. 16, 1975

[51] Int. Cl.[2] ..... A01H 5/00

[52] U.S. Cl. ..... Plt./22

[58] Field of Search ..... Plt./1, 22

*Primary Examiner*—Robert E. Bagwill

*Attorney, Agent, or Firm*—Klarquist, Sparkman, Campbell, Leigh, Hall & Whinston

CLAIM

A new and distinct cultivar of rose plant, substantially as herein shown and described, characterized particularly as to novelty by its generally upright habit of growth, each main branch from the plant base terminating at first blooming in long stemmed broad, rounded clusters of blooms, the secondary growth after first blooming usually producing flowers borne one to a stem, the flowers having little or no fragrance, being bicolor, the petals being Blood Red on upper side and near white on lower, and being resistant to rose powdery mildew.

1 Drawing Figure

1

This present invention relates to a new and distinct cultivar of rose plant which was originated by me by crossing two unnamed cultivars.

The primary objective of this breeding was to develop a new rose cultivar with a plant habit that would produce large clusters of flowers on long stems, approximately 12 inches, as well as normal short stemmed clusters and singly borne flowers. This objective was substantially achieved along with other desirable improvements as evidenced by the following unique combination of characteristics which are outstanding in the new cultivar and which distinguish it from its parents as well as from all other cultivars of which I am aware:

1. A generally upright habit of growth.
2. Each main branch from the base of the plant terminates in long stemmed clusters carried at such an angle and length as to make a broad rounded cluster of blooms.
3. Secondary growth produced after the first flowering usually produces flowers borne one to a stem.
4. A bicolor flower that is Blood Red on upper side of petals, near white on lower side.
5. Little or no fragrance.
6. A strong tendency to resist rose powdery mildew.

Asexual reproduction of this new cultivar by budding, as performed at Wasco, Calif., show that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with *Wilson's Horticultural Color Chart*, except where ordinary dictionary significance of color is indicated.

Parentage: Seedling.

*Seed Parent.*—Unnamed cultivar.

*Pollen Parent.*—Unnamed cultivar.

Classification:

*Botanical.*—Rosa hybrid.

2

FLOWER

Observations made from specimens grown at Irvine, Calif., September 1975.

Blooming habit: Continuous.

Bud:

*Size.*—Approximately ¾″ when petals start to unfurl.

*Form.*—Pointed ovoid.

*Color.*—When sepals first divide—near white except where first exposed to sun is near Blood Red (820). When half blown; upper side of petals near Blood Red (820). Lower side of petals near white with streaks of Blood Red (820).

*Sepals.*—Color: Outer surface near Spinach Green (0960/3) with some shading of Garnet Brown (00918/3). Inner surface near Spinach Green (0960/3) with some white tomentum. Three appendaged sepals, normally appendaged. Two unappendaged sepals hairy edged.

*Receptacle.*—Color: Near Spinach Green (0960/3) with some shading of Garnet Brown (00918/3). Shape: Funnel. Size: Large, relative to flower size.

*Peduncle.*—Length: Medium, to short. Surface: Prickly. Color: Bronzy. Strength: Stiff, slender.

*Opening.*—Petal edges only slightly curled.

Bloom:

*Size.*—Medium. Average open size 2–2½″.

*Borne.*—Some singly, mostly in clusters of long stems. If in clusters—Rounded.

*Stems.*—Long.

*Form.*—When first open, high centered. Permanence: outer petal edges slightly curl.

*Petalage.*—Number of petals under normal conditions—20–25.

*Color.*—Center of flower: upper side of petals near Blood Red (820). Reverse side of petals near white with occasional streaks of Blood Red (860/3). Base of petals: small area of near Buttercup yellow (5/1). General tonality from a distance near Blood Red (860) when viewed from above—Bicolor characteristic evident when viewed from side or below.

*Discoloration.*—General tonality at end of first day: Same as freshly opened. Third day: Color is only slightly darker and less glossy.

*Fragrance.*—Little to none.

Petals:

*Textrue.*—Thick. Quite stiff or rigid.

*Shape.*—Round.

*Form.*—Tips slightly recurved.

*Arrangement.*—Loosely imbricated. Petaloids in center; few.

*Persistence.*—Drop off cleanly.

*Lastingness.*—On the plant—long. As cut flower—long.

Reproductive Parts:

*Anthers.*—Medium. Color—Near Buttercup yellow (5/2). Arrangement—regular around styles.

*Filaments.*—Near Primrose yellow (601).

*Pollen.*—Lemon yellow.

*Styles.*—Color—Distal half near Rose Madder (23). Basal half near white.

*Stigmas.*—Color—Near white.

PLANT

Form: Bush.

Growth: Very vigorous, upright, branching.

Foliage:

*Size.*—Medium.

*Quantity,*—Normal.

*Color.*—New foliage: Near Garnet Brown (00918/3). Old Foliage: Near Spinach green (0960). Number of leaflets on normal mid-stem leaves: 5.

Leaflets:

*Shape.*—Oval pointed.

*Texture.*—Upper side—leathery.

*Edge.*—Serrated.

*Serration.*—Single, small.

*Petiole.*—Rachis—Color—reddish. Underside—prickles.

*Stipules.*—Long, bearded.

*Disease Resistance.*—Normally resistant to mildew under normal growing conditions at Irvine, Calif.

Stems and branches:

*New Stems.*—Color—Garnet Brown (00918).

*Bark.*—Smooth.

*Old Wood.*—Color—Green.

*Bark.*—Smooth.

Prickles:

*Quantity.*—On main stalks from base—ordinary. On laterals from stalk—ordinary.

*Form.*—Narrow base, hooked downward.

*Color When Young.*—Garnet Brown (00918).

*Position.*—Irregular.

Small prickles:

*Quantity.*—On main stalks—few. On laterals—few.

*Color.*—Brown.

I claim:

1. A new and distinct cultivar of rose plant, substantially as herein shown and described, characterized particularly as to novelty by its generally upright habit of growth, each main branch from the plant base terminating at first blooming in long stemmed broad, rounded clusters of blooms, the secondary growth after first blooming usually producing flowers borne one to a stem, the flowers having little or no fragrance, being bicolor, the petals being Blood Red on upper side and near white on lower, and being resistant to rose powdery mildew.

* * * * *

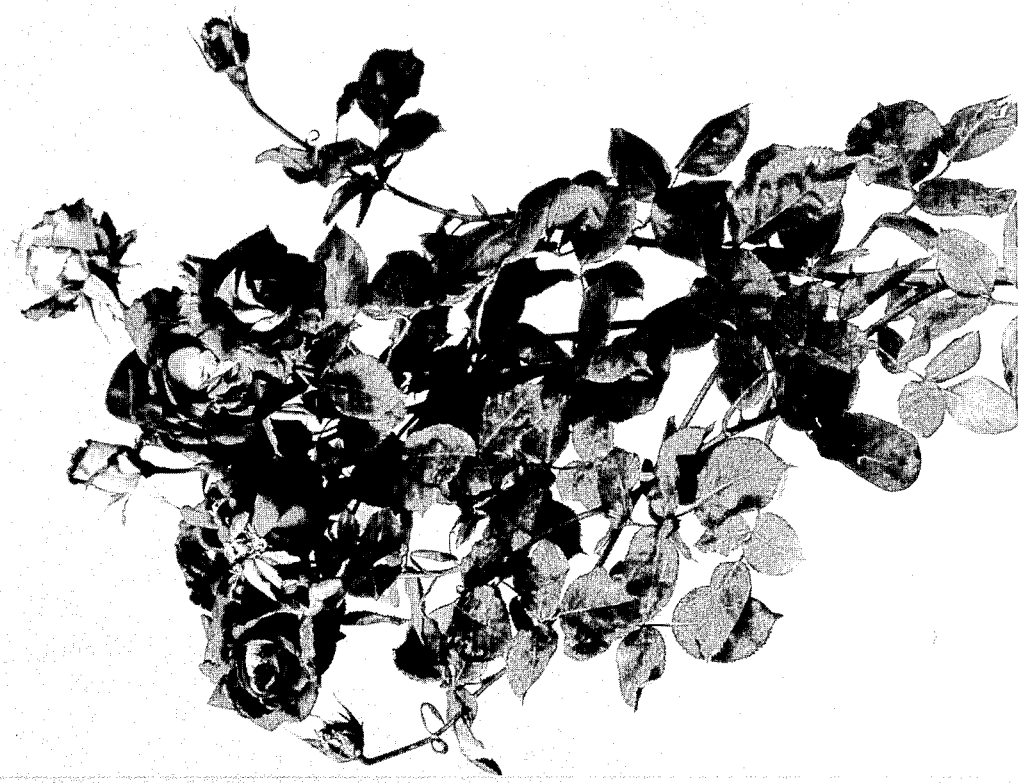
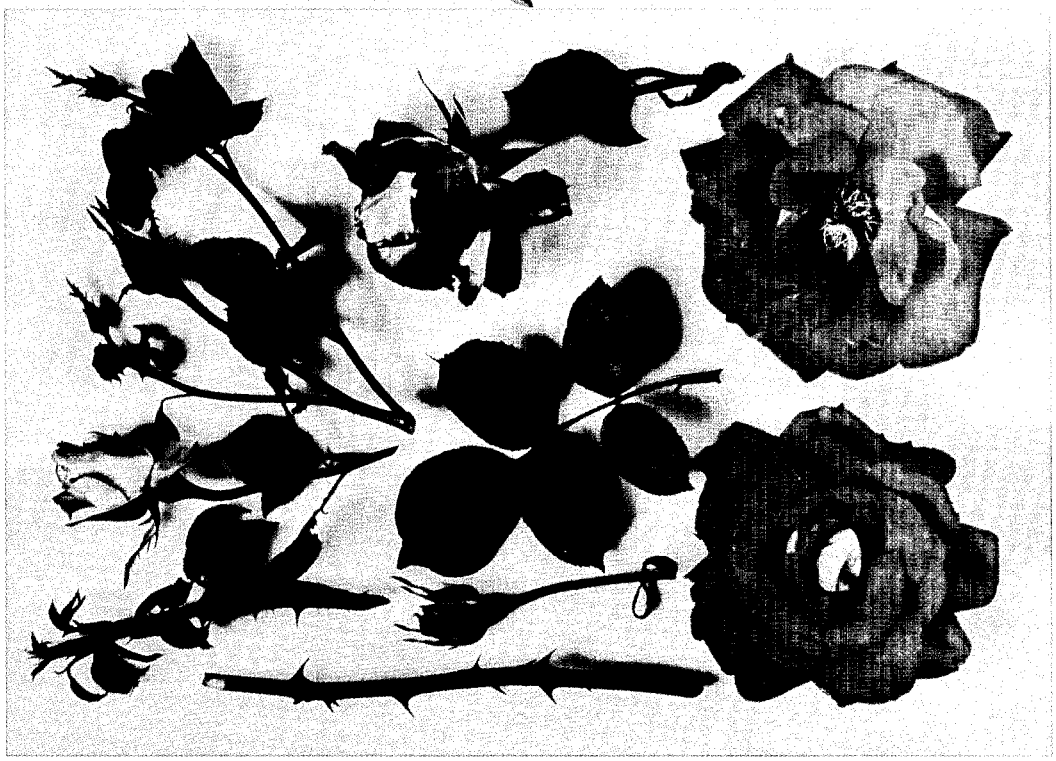

Dec. 21, 1976 W. A. WARRINER Plant Pat. 3,995
ROSE PLANT
Filed Oct. 16, 1975